United States Patent [19]

Dostert et al.

[11] 4,003,915
[45] Jan. 18, 1977

[54] TRICYCLIC IMINES

[75] Inventors: Philippe Dostert, Versailles, France; Emilio Kyburz, Reinach, Switzerland

[73] Assignee: Hoffmann-La Roche Inc., Nutley, N.J.

[22] Filed: June 19, 1975

[21] Appl. No.: 588,268

Related U.S. Application Data

[62] Division of Ser. No. 433,318, Jan. 14, 1974, Pat. No. 3,905,972, which is a division of Ser. No. 184,901, Sept. 29, 1971, Pat. No. 3,803,234.

[30] Foreign Application Priority Data

Oct. 9, 1970 Switzerland .................. 14972/70

[52] U.S. Cl. .......................................... 260/327 B
[51] Int. Cl.² .................................... C07D 337/12
[58] Field of Search ................. 260/327 B, 333

[56] References Cited

UNITED STATES PATENTS 3,594,392  7/1971  Winthrop .................. 260/327

FOREIGN PATENTS OR APPLICATIONS

| 238,720 | 2/1965 | Austria | 260/327 |
| 626,301 | 6/1965 | Belgium | 260/327 |
| 2,154,456 | 11/1973 | France | 260/327 |
| 1,543,578 | 9/1969 | Germany | 260/327 |
| 2,150,079 | 4/1972 | Germany | 260/327 B |

*Primary Examiner*—Henry R. Jiles
*Assistant Examiner*—C.M.S. Jaisle
*Attorney, Agent, or Firm*—Samuel L. Welt; Bernard S. Leon; William G. Isgro

[57] ABSTRACT

Tricyclic imines of the formula

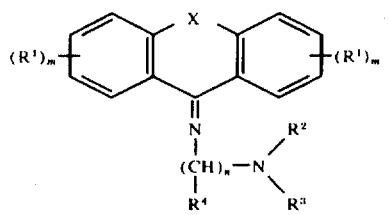

wherein $R^1$, $R^2$, $R^3$, $R^4$, X, m and n are as hereinafter described, prepared from the corresponding ketones of the formula

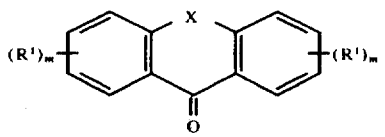

wherein $R^1$, X and m are as hereinafter described, are disclosed. The compounds of formula I are useful as antidepressants, as well as anticonvulsants and agents for the treatment of Parkinsonism.

3 Claims, No Drawings

TRICYCLIC IMINES

CROSS-REFERENCE TO RELATED APPLICATIONS

This application is a division of U.S. Pat. application Ser. No. 433,318, filed Jan. 14, 1974, now U.S. Pat. No. 3,905,972, which in turn is a division of U.S. Pat. Application Ser. No. 184,901, filed Sept. 29, 1971, now U.S. Pat. No. 3,803,234, issued Apr. 9, 1974.

BRIEF SUMMARY OF THE INVENTION

The invention relates to compounds of the formula

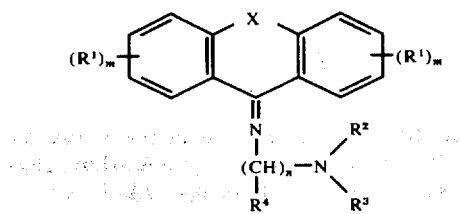

wherein X is oxymethylene or thiomethylene; $R^1$ is hydrogen, halogen, hydroxy, lower alkoxy, lower alkyl, cyano, lower alkoxycarbonyl, carbamoyl, sulfamoyl, lower alkylmercapto, trifluoromethyl or nitro; $R^2$ and $R^3$, individually, are hydrogen or lower alkyl, or $R^2$ and $R^3$, together with the nitrogen atom, are a monocyclic, saturated 5- or 6-membered heterocyclic group which may contain an oxygen or sulfur atom or an additional nitrogen atom; $R^4$ is hydrogen or lower alkyl; m is an integer from 1 to 3; and $n$ is an integer from 2 to 5, and the pharmaceutically acceptable acid addition salts thereof. The compounds of formula I are useful as antidepressants, as well as anticonvulsants and as agents for the treatment of Parkinsonism.

In another aspect, the invention relates to intermediates of the formula

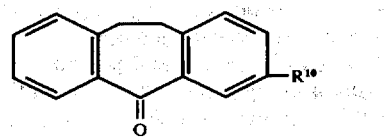

wherein $R^{10}$ is cyano or lower alkoxycarbonyl.

In yet another aspect, the invention relates to intermediates of the formula

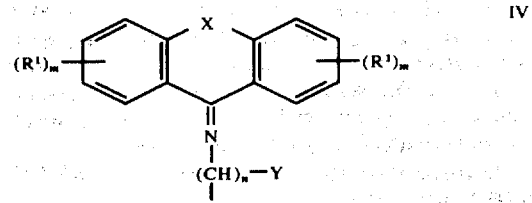

wherein $R^1$, $R^4$, X, $m$ and $n$ are as previously described and Y is halogen, lower alkylsulfonyloxy, phenylsulfonyloxy, or phenylsulfonyloxy substituted by lower alkyl or halogen.

DETAILED DESCRIPTION OF THE INVENTION

The invention relates to compounds of the formula

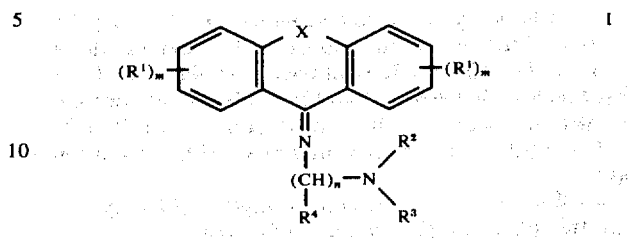

wherein X is sulfur, oxymethylene, thiomethylene, ethylene, lower alkanoylamido substituted ethylene, vinylene or vinylene substituted by halogen, lower alkyl, cyano or sulfamoyl; $R^1$ is hydrogen, halogen, hydroxy, lower alkoxy, lower alkyl, cyano, lower alkoxycarbonyl, carbamoyl, sulfamoyl, lower alkylmercapto, trifluoromethyl or nitro; $R^2$ and $R^3$, individually, are hydrogen or lower alkyl, or $R^2$ and $R^3$, together with the nitrogen atom, are a monocyclic, saturated 5- or 6-membered heterocyclic group which may contain an oxygen or sulfur atom or an additional nitrogen atom; $R^4$ is hydrogen or lower alkyl, m is an integer from 1 to 3; and n is an integer from 2 to 5, and the pharmaceutically acceptable acid addition salts thereof.

As used herein, the term "lower alkyl" denotes a straight or branched chain saturated hydrocarbon group containing from 1-6 carbon atoms, for example, methyl, ethyl, propyl, isopropyl, butyl, t-butyl, neopentyl, pentyl, hexyl, and the like. The term "lower alkoxy" denotes an alkyl ether group in which the lower alkyl group is as described above, for example, methoxy, ethoxy, propoxy, pentoxy, and the like. The term "halogen" denotes all the halogens, i.e., bromine, chlorine, fluorine and iodine; of these, fluorine, chlorine and bromine are preferred. The term "lower alkanoylamido" denotes a radical wherein the alkanoyl group is derived from an aliphatic carboxylic acid, e.g., an alkanecarboxylic acid, of 1–6 carbon atoms, for example, formyl, acetyl, propionyl, and the like. The carbamoyl and sulfamoyl groups can be optionally mono- or di-substituted by lower alkyl, for example, mono-methyl or di-methylaminocarbonyl, monomethyl or diethylaminosulfonyl, and the like. The monocyclic, saturated 5- or 6-membered heterocyclic groups formed by $R^2$ and $R^3$ and the nitrogen atom to which they are attached can be pyrrolidino, piperidino, piperazino, morpholino, thiamorpholino, and the like, as well as the corresponding groups which are substituted by lower alkyl, lower alkoxyalkyl, amino or lower alkylamino.

A preferred subgenus of the tricyclic imines of the invention comprises compounds of the formula

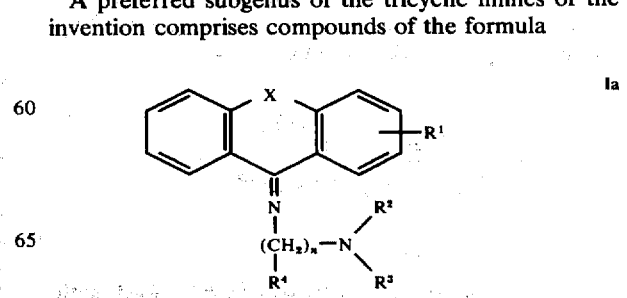

wherein X, R¹, R², R³, R⁴ and n are as previously described,
and the pharmaceutically acceptable acid addition salts thereof.

A particularly preferred subgenus of the tricyclic imines of the invention comprises the compounds of formula Ia, wherein X is ethylene or vinylene, R¹ is hydrogen or halogen, R² and R³, individually, are hydrogen or lower alkyl, R⁴ is hydrogen and n is 2 or 3.

The most preferred tricyclic imines of the invention are:

3-chloro-N-(2-dimethylamino-ethyl)-10,11-dihydro5H-dibenzo[a,d]cyclohepten-5-imine;

1-chloro-N-(2-dimethylamino-ethyl)-10,11-dihydro-5H-dibenzo[a,d]cyclohepten-5-imine;

N-(2-dimethylamino-ethyl)-10,11-dihydro-5H-dibenzo[a,d]cyclohepten-5-imine; and 1-bromo-N-(2-dimethylamino-ethyl)-10,11-dihydro-5H-dibenzo[a,d]cyclohepten-5-imine.

Exemplary of the compounds of formula I are:

N-(3-ethylamino-propyl)-10,11-dihydro-5H-dibenzo-[a,d]cyclohepten-5-imine;

N-(2-dimethylamino-ethyl)-10,11-dihydro-5H-dibenzo-[a,d]cyclohepten-5-imine;

N-(3-ethylamino-propyl)-5H-dibenzo[a,d]cyclohepten-5-imine;

N-(2-dimethylamino-ethyl)-5H-dibenzo[a,d]cyclohepten-5-imine;

3-chloro-N-(2-dimethylamino-ethyl)-10,11-dihydro-5H-dibenzo[a,d]cyclohepten-5-imine;

1-chloro-N-(2-dimethylamino-ethyl)-10,11-dihydro-5H-dibenzo[a,d]cyclohepten-5-imine;

1-bromo-N-(2-dimethylamino-ethyl)-10,11-dihydro-5H-dibenzo [a,d]cyclohepten-5-imine;

1-methyl-N-(3-diethylamino-propyl)-10,11-dihydro-5H-dibenzo [a,d]cyclohepten-5-imine;

1-cyano-N-(2-dimethylamino-ethyl)-10,11-dihydro-5H-dibenzo [a,d]cyclohepten-5-imine;

10-bromo-N-(2-dimethylamino-ethyl)-5H-dibenzo[a,d]cyclohepten-5-imine;

2-chloro-N-(3-diethylamino-propyl)-thioxanthen-9-imine;

10-cyano-N-(2-dimethylamino-ethyl)-5H-dibenzo[a,d]cyclohepten-5-imine;

10-acetamido-N-(2-dimethylamino-ethyl)-5H-dibenzo[a,d]cyclohepten-5-imine;

3-chloro-N-(2-morpholino-ethyl)-10,11-dihydro-5H-dibenzo [a,d]cyclohepten-5-imine;

3-chloro-N-[2-(4-methyl-piperazino)-ethyl]-10,11-dihydro-5H-dibenzo[a,d]cyclohepten-5-imine;

1-chloro-N-(2-dimethylamino-1-methyl-ethyl)-10,11-dihydro-5H-dibenzo[a,d]cyclohepten-5-imine;

1-chloro-N-(2-amino-ethyl)-10,11-dihydro-5H-dibenzo[a,d]cyclohepten-5-imine; and the like.

The compounds of formula I and their pharmaceutically acceptable acid addition salts can be prepared by reacting a ketone of the formula

II wherein X, R¹ and m are as previously described, with a diamine of the formula

III wherein R², R³, R⁴ and n are as previously described, or by reacting a compound of the formula

IV wherein X, R¹, R⁴, m and n are as previously described and Y is halogen, lower alkylsulfonyloxy, phenylsulfonyloxy or phenylsulfonyloxy substituted by lower alkyl or halogen, with an amine of the formula

V wherein R² and R³ are as previously described, and, if desired, converting a compound of formula I so obtained into a pharmaceutically acceptable acid addition salt.

According to one process embodiment of the invention, the compounds of formula I are prepared by reacting a ketone of formula II with a diamine of formula III.

The ketone starting materials of formula II are, in general, known. A novel ketone starting material of formula II is 3-cyano-10,11-dihydro-5H-dibenzo[a,d]cyclohepten-5-one, which can be prepared in a known manner, for example, by treating the corresponding ketone which is substituted in the 3-position by a halogen atom, preferably by a bromine atom, with a cyanide, preferably, copper cyanide, conveniently in a solvent such as, for example, dimethylformamide and the like. The 3-(lower alkoxycarbonyl)-10,11-dihydro-5H-dibenzo[a,d]cyclohepten-5-one starting materials of formula II, for example, 3-methoxycarbonyl10,11-dihydro-5H-dibenzo[a,d]cyclohepten-5-one, are also novel. They can be prepared from the corresponding ketone, which is substituted in the 3-position by a cyano group, by saponification in a known manner and esterification of the resulting ketone which is substituted in the 3-position by a carboxyl group. The novel ketone starting materials of formula II hereinbefore also form part of the present invention.

The diamine starting materials of formula III are known compounds.

The reaction of a ketone of formula II with a diamine of formula III can be carried out by heating. Preferably, they are heated together at a temperature at which no decomposition occurs; that is, at a temperature in the range of between about 50° and about 250° C. It is advisable to carry out this thermal reaction under an atmosphere of an inert gas, such as, nitrogen, argon or the like.

A ketone of formula II can, however, also be reacted with a diamine of formula III with the aid of a neutral or acidic dehydrating agent. Preferred neutral dehydrating agents are the so-called molecular sieves which are ion-exchangers having wide internal pores accessible only through relatively narrow channels; for example, synthetic zeolite, sodium aluminum silicate, calcium aluminum silicate and the like. As the acidic dehydrating agent, generally, there can be used Lewis acids, preferably the halides of an element from Group III, IV, V or VIII of the Periodic System. Examples of such Lewis acids are, from Group III, boron trifluoride and aluminum trichloride, from Group IV titanium tetrachloride and germanium tetrachloride, and from Group V arsenic trichloride, antimony trichloride and antimony pentachloride. Of these Lewis acids, titanium tetrachloride and antimony trichloride are preferred.

When a ketone of formula II is reacted with a diamine of formula III with the aid of a neutral dehydrating agent, there is advantageously used one of the aforementioned ion-exchangers having a pore diameter of about 4A and a granular size of about 2 mm. This reaction is conveniently carried out by heating a mixture of the reactants together with the chosen ion-exchanger, acting as the molecular sieve, expediently with the addition of a solvent, preferably a hydrocarbon such as benzene or toluene, at a temperture in the range of between about room temperature and the boiling point of the reaction mixture.

The reaction of a ketone of formula II with a diamine of formula III with the aid of one of the aforementioned Lewis acids is conveniently carried out by allowing the reactants to react with the chosen Lewis acid at a temperature in the range of between about room temperature and the boiling point of the reaction mixture in the presence of a solvent. It has proven advantageous to carry out this reaction under an atmosphere of an inert gas, for example, under nitrogen, argon, or the like.

In the foregoing reaction, the choice of the solvent is dependent on the solubility of the reactants. Suitable solvents are, for example, cyclic hydrocarbons such as cyclohexane, benzene, toluene, mesitylene or the like, and chlorinated hydrocarbons, preferably, methylene chloride. Under certain circumstances, the diamine of formula III can itself serve as the solvent. Similarly, the Lewis acid used as the acidic dehydrating agent is conveniently utilized in solution. The solvent used for the ketone can expediently be utilized as the solvent for the Lewis acid. When titanium tetrachloride, for example, is used as the acidic dehydrating agent, benzene or toluene is preferably used as the solvent.

The oxide of the dehydrating agent which is formed in the reaction is removed by decantation or filtration. It can, if desired, be converted to the corresponding halide which can again be employed as the dehydrating agent. The filtrate is concentrated. The concentrate is diluted with water and extracted with a solvent suitable for the extraction of the compound of formula I, of which ether is particularly preferred. The compound of formula I which is isolated from the extract, generally an oil, crystallizes after a short time.

According to the second embodiment of the process of the invention, the compounds of formula I are prepared by reacting a compound of formula IV with an amine of formula V.

The compounds of formula IV are novel and form part of this invention. They can be prepared, for example, by condensing the corresponding tricyclic ketone, which may be ring-substituted for example, 10,11-dihydro-5H-dibenzo[a,d]cyclohepten-5-one, with an amine corresponding to the side-chains that are to be introduced, for example, ethanolamine, in a known manner, expediently at an elevated temperature. In the case of the specific examples just mentioned, halogenating, mesylating or tosylating the resulting N-(2-hydroxyethyl)-10,11-dihydro-5H-dibenzo[a,d]cyclohepten-5-imine in a known manner, for example, using p-toluenesulfonyl chloride conveniently in an organic solvent, for example, a hydrocarbon such as benzene or the like, at room temperature.

The amines of formula V are known compounds.

The reaction of a compound of formula IV with an amine of formula V can be readily carried out. Thus, the reaction can be carried out, if desired, in the presence of an acid-binding agent, for example, potassium carbonate, sodium carbonate or the like, conveniently in an organic solvent, for example, a lower alkanol such as ethanol or the like, or a cyclic hydrocarbon such as toluene, xylene or the like, at a temperature in the range of between room temperature and the boiling point of the reaction mixture.

The compounds of formula I readily form acid addition salts by treatment with acids, for example, with hydrohalic acids such as hydrochloric acid, hydrobromic acid and the like, with other mineral acids such as sulfuric acid and the like. Treatment with one equivalent of acids yields mono-salts, with two equivalents of acid di-salts are formed. Treatment with organic acids, such as benzoic acid, acetic acid, oxalic acid, citric acid, lactic acid, maleic acid and the like usually yields mono-salts. The oxalates crystallize particularly well.

Ring-substituted compounds of formula I are obtained as mixtures of the two stereoisomers. If desired, the stereoisomeric forms can be separated, for example, by fractional crystallization or by chromatography.

A preferred embodiment of the foregoing process comprises reacting a ketone of the formula

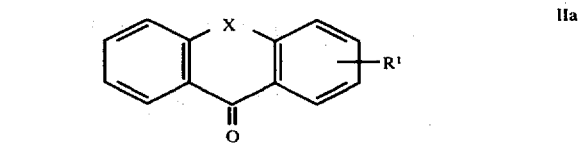

IIa wherein X and $R^1$ are as hereinbefore described, with a diamine of formula III with the aid of a Lewis acid, optionally in the presence of a solvent, and, if desired, converting the compound of formula I obtained into an acid addition salt. A preferred aspect of this embodiment comprises using a ketone of formula IIa in which X is ethylene or vinylene and $R^1$ is hydrogen or halogen and a diamine of formula III wherein $R^2$ and $R^3$, individually, are hydrogen or lower alkyl, $R^4$ is hydrogen and $n$ is 2 or 3.

The compounds of formula I and their pharmaceutically acceptable acid addition salts are pharmacodynamically active. In particular, they possess neuropsychotropic properties. Most of the compounds of formula I exhibit antidepressant activity, as well as anticonvulsant and anti-Parkinson activity and are therefore useful as antidepressants as well as anticonvulsants and antiParkinson agents, in the treatment of depression, convulsions and Parkinsonism. Some compounds of formula I possess antitussive and diuretic properties, and are therefore useful as antitussive agents and diuretics. Most interesting of the compounds of formula I are:

1-chloro-N-(2-dimethylamino-ethyl)-10,11-dihydro-5H-dibenzo[a,d]cyclohepten-5-imine, which acts principally as an antidepressant and has very weak anticholinergic activity; N-(2-dimethylamino-ethyl)-10,11-dihydro-5H-dibenzo[a,d]cyclohepten-5-imine, which has strong central and peripheral anticholinergic activity and 3-chloro-N-(2-dimethylamino-ethyl)-10,11-dihydro5H-dibenzo[a,d]cyclohepten-5-imine, which has strong antidepressant and anticholinergic activity, the last-mentioned compounds are very active against Parkinsonism; 1-Bromo-N-(2-dimethylaminoethyl)-10,11-dihydro-5H-dibenzo[a,d]cyclohepten-5-imine which possesses strong anticonvulsant properties; 3-chloro-N-(2-diethylamino-ethyl)-10,11-dihydro-5H-dibenzo[a,d]cyclohepten-5-imine, which has strong antitussive activity; and 1-chloro-(2-diethylamino-ethyl)-10,11-dihydro-5H-dibenzo[a,d]cyclohepten-5-imine, which has strong diuretic activity.

The toxicity of the compounds of formula I is very low, for example, 1-chloro-N-(2-dimethylamino-ethyl)-10,11-dihydro5H-dibenzo[a,d]cyclohepten-5-imine and 1-bromo-N-(2-dimethylaminoethyl)-10,11-dihydro-5H-dibenzo[a,d]cyclohepten-5-imine have demonstrated an $LD_{50}$ of about 750 mg/kg. in mice on oral administration. In rats, anticonvulsant activity is evident at a dosage of 30 mg. p.o./kg.

Compounds of formula I in which X is an ethylene or vinylene group and $R^1$ is hydrogen or halogen are preferred compounds of the invention.

The compounds of formula I and their pharmaceutically acceptable acid addition salts can be used for the treatment of illnesses of different etiology. They can be used in the form of pharmaceutical preparations which contain them in association with a compatible pharmaceutical carrier. The carrier can be an organic or inorganic inert carrier which is suitable for enteral or parenteral administration such as, for example, water, gelatin, gum arabic, lactose, starches, vegetable oils, polyalkylene glycols, and the like. The pharmaceutical preparations can be made up in solid form, for example, tablets, dragees, suppositories or capsules, or in liquid form, for example, solutions, suspensions or emulsions. The preparations can be sterilized and/or can contain adjuvants such as preserving, stabilizing, wetting or emulsifying agents or salts for varying the osmotic pressure. They can also contain yet other therapeutically active substances.

The amount of a compound of formula I administered to warm-blooded animals varies within a wide range according to the individual compound and to the specific needs of the warm-blooded animal being treated. However, in general, the daily dose for oral administration comprises from about 50 mg. to about 200 mg. of a compound of formula I.

The following examples further illustrate the invention. All parts are by weight and all temperatures are in degrees Centigrade, unless otherwise mentioned.

Example 1

Preparation of 3-chloro-N-(2-dimethylamino-ethyl)-10,11-dihydro5H-dibenzo[a,d]cyclohepten-5-imine oxalate 12.1 g. of 3-chloro-10,11-dihydro-5H-dibenzo[a,d]cyclohepten-5-one are dissolved in 300 ml. of absolute benzene at room temperature under an atmosphere of argon with stirring. Following the addition of 44 g. of N,N-dimethylamino-ethylamine, the solution is cooled to 0° C. and treated dropwise with a solution containing 3.6 g. of titanium tetrachloride in 40 ml. of absolute benzene. The reaction mixture is stirred at room temperature for 48 hours and then filtered. The filtrate is concentrated under reduced pressure. The concentrate is treated with ice and 3N hydrochloric acid. The unreacted ketone is taken up in ether. Thereafter, the aqueous phase is made alkaline and extracted with ether. The ether extract is washed with a saturated aqueous sodium chloride solution, dried over sodium sulfate and evaporated. The 3-chloro-N-(2-dimethylaminoethyl)-10,11-dihydro-5H-dibenzo[a,d]cyclohepten-5-imine which is obtained is taken up in acetone and treated with a solution containing 2.8 g. of oxalic acid in 40 ml. of ethanol. The oxalate which precipitates in crystalline form melts at 200°–202° C. after recrystallization from acetone/methanol.

The 3-chloro-N-(2-dimethylamino-ethyl)-10,11-dihydro-5H-dibenzo[a,d]cyclohepten-5-imine oxalate is obtained as a stereoisomeric mixture in the ratio of about 3:1. The two isomers can be separated by thin layer chromatography [adsorbent: aluminum oxide Merck F 254, eluting agent: acetone/toluene/diethylamine (49:49:2)].

In an analogous manner, utilizing the procedure of Example 1:

from 3-chloro-10,11-dihydro-5H-dibenzo[a,d]cyclohepten5-one and N,N-diethylamino-ethylamine, there is obtained 3-chloro-N-(2-diethylamino-ethyl)-10,11-dihydro-5H-dibenzo[a,d]cyclohepten-5-imine, melting point 90°–92° C. (oxalate);

from 3-chloro-10,11-dihydro-5H-dibenzo[a,d]cyclohepten-5-one and N,N-dimethylamino-propylamine, there is obtained 3-chloro-N-(3-dimethylamino-propyl)-10,11-dihydro-5H-dibenzo[a,d]cyclohepten-5-imine, melting point 180°–182° C. (oxalate);

from 3-chloro-10,11-dihydro-5H-dibenzo[a,d]cyclohepten-5-one and N,N-diethylamino-propylamine, there is obtained 3-chloro- N-(3-diethylamino-propyl)-10,11-dihydro-5H-dibenzo[a,d]cyclohepten-5-imine, melting point 143°–145° C. (oxalate);

from 1-chloro-10,11-dihydro-5H-dibenzo[a,d]cyclohepten-5-one and N,N-dimethylamino-ethylamine, there is obtained 1-chloro-N-(2-dimethylamino-ethyl)-10,11-dihydro-5H-dibenzo[a,d]cyclohepten-5-imine, melting point 187°–189° C. (oxalate);

from 1-chloro-10,11-dihydro-5H-dibenzo[a,d]cyclohepten-5-one and N,N-dimethylamino-propylamine, there is obtained 1-chloro-N-(3-dimethylamino-propyl)-10,11-dihydro-5H-dibenzo[a,d]cyclohepten-5-imine, melting point 159°–161° C. (oxalate);

from 1-chloro-10,11-dihydro-5H-dibenzo[a,d]cyclohepten-5-one and N,N-diethylamino-ethylamine, there is obtained 1-chloro-N-(2-diethylamino-ethyl)-10,11-dihydro-5H-dibenzo[a,d]cyclohepten-5-imine, melting point 137°–139° C. (oxalate);

from 1-chloro-10,11-dihydro-5H-dibenzo[a,d]cycloheptatan-5-one and N,N-diethylamino-propylamine, there is obtained 1-chloro-N-(3-diethylamino-propyl)-10,11-dihydro-5H-dibenzo[a,d]cyclohepten-5-imine, melting point 162°–164° C. (oxalate);

from 1-bromo-10,11-dihydro-5H-dibenzo[a,d]cyclohepten-5-one and N,N-dimethylamino-ethylamine, there is obtained 1-bromo-N-(2-dimethylamino-ethyl)-10,11-dihydro-5H-dibenzo[a,d]cyclohepten-5-imine, melting point 193°–195° C. (oxalate);

from 1-bromo-10,11-dihydro-5H-dibenzo[a,d]cyclohepten-5-one and N,N-dimethylamino-propylamine, there is obtained 1-bromo-N-(3-dimethylamino-propyl)-10,11-dihydro-5H-dibenzo[a,d]cyclohepten-5-imine, melting point 142°–145° C. (oxalate);

from 1-bromo-10,11-dihydro-5H-dibenzo[a,d]cyclohepten-5-one and N,N-diethylamino-propylamine, there is obtained 1-bromo-N-(3-diethylamino-propyl)-10,11-dihydro-5H-dibenzo[a,d]cyclohepten-5-imine, melting point 148°–150° C. (oxalate);

from 1-methyl-10,11-dihydro-5H-dibenzo[a,d]cyclohepten-5-one and N,N-dimethylamino-ethylamine, there is obtained 1-methyl-N-(2-dimethylamino-ethyl)-10,11-dihydro-5H-dibenzo[a,d]cyclohepten-5-imine, melting point 186°–188° C. (oxalate);

from 1-methyl-10,11-dihydro-5H-dibenzo[a,d]cyclohepten-5-one and N,N-dimethylamino-propylamine, there is obtained 1-methyl-N-(3-dimethylamino-propyl)-10,11-dihydro-5H-dibenzo[a,d]cyclohepten-5-imine, melting point 160°–163° C. (oxalate);

from 1-methyl-10,11-dihydro-5H-dibenzo[a,d]cyclohepten-5-one and N,N-diethylamino-ethylamine, there is obtained 1-methyl-N-(2-diethylamino-ethyl)-10,11-dihydro-5H-dibenzo[a,d]cyclohepten-5-imine, melting point 133°–136° C. (oxalate);

from 1-methyl-10,11-dihydro-5H-dibenzo[a,d]cyclohepten-5-one and N,N-diethylamino-propylamine, there is obtained 1-methyl-N-(3-diethylamino-propyl)-10,11-dihydro-5H-dibenzo[a,d]cyclohepten-5-imine, melting point 155°–157° C. (oxalate);

from 1-cyano-10,11-dihydro-5H-dibenzo[a,d]cyclohepten-5-one and N,N-dimethylamino-ethylamine, there is obtained 1-cyano-N-(2-dimethylamino-ethyl)-10,11-dihydro-5H-dibenzo[a,d]cyclohepten-5-imine, melting point 200°–202° C. (oxalate);

from 1-cyano-10,11-dihydro-5H-dibenzo[a,d]cyclohepten-5-one and N,N-dimethylamino-propylamine, there is obtained 1-cyano-N-(3-dimethylamino-propyl)-10,11-dihydro-5H-dibenzo[a,d]cyclohepten-5-imine, melting point 162°–164° C. (oxalate);

from 1-cyano-10,11-dihydro-5H-dibenzo[a,d]cyclohepten-5-one and N,N-diethylamino-propylamine, there is obtained 1-cyano-N-(3-diethylamino-propyl)-10,11-dihydro-5H-dibenzo[a,d]cyclohepten-5-imine, melting point 159°–161° C. (oxalate);

from 10,11-dihydro-5H-dibenzo[a,d]cyclohepten-5-one and N,N-dimethylamino-ethylamine, there is obtained N-(2-dimethylamino-ethyl)-10,11-dihydro-5H-dibenzo[a,d]cyclohepten-5-imine, melting point 188°–190° C. (oxalate);

from 10,11-dihydro-5H-dibenzo[a,d]cyclohepten-5-one and N,N-dimethylamino-propylamine, there is obtained N-(3-dimethylamino-propyl)-10,11-dihydro-5H-dibenzo[a,d]cyclohepten-5-imine, melting point 150°–152° C. (oxalate);

from 10,11-dihydro-5H-dibenzo[a,d]cyclohepten-5-one and N,N-diethylamino-ethylamine, there is obtained N-(2-diethylamino-ethyl)-10,11-dihydro-5H-dibenzo[a,d]cyclohepten-5-imine, melting point 130°–132° C. (oxalate);

from 10,11-dihydro-5H-dibenzo[a,d]cyclohepten-5-one and N,N-diethylamino-propylamine, there is obtained N-(3-diethylamino-propyl)-10,11-dihydro-5H-dibenzo[a,d]cyclohepten-5-imine, melting point 153°–155° C. (oxalate);

from 10,11-dihydro-3-methyl-5H-dibenzo[a,d]cyclohepten-5-one and N,N-dimethylamino-ethylamine, there is obtained N-(2-dimethylamino-ethyl)-3-methyl-10,11-dihydro-5H-dibenzo[a,d]cyclohepten-5-imine, melting point 172°–175° C. (oxalate);

from 10,11-dihydro-2-methoxy-5H-dibenzo[a,d]cyclohepten-5-one and N,N-dimethylamino-ethylamine, there is obtained N-(2-dimethylamino-ethyl)-2-methoxy-10,11-dihydro-5H-dibenzo[a,d]cyclohepten-5-imine, melting point 123°–126° C. (oxalate);

from 10,11-dihydro-3-nitro-5H-dibenzo[a,d]cyclohepten-5-one and N,N-dimethylamino-ethylamine, there is obtained N-(2-dimethylamino-ethyl)-3-nitro-10,11-dihydro-5H-dibenzo[a,d]cyclohepten-5-imine, melting point 126°–129° C. (oxalate);

from 10,11-dihydro-1-methylthio-5H-dibenzo[a,d]cyclohepten-5-one and N,N-dimethylamino-ethylamine, there is obtained N-(2-dimethylamino-ethyl)-1-methylthio-10,11-dihydro-5H-dibenzo[a,d]cyclohepten-5-imine, melting point 146°–149° C. (oxalate);

from 3-chloro-10,11-dihydro-5H-dibenzo[a,d]cyclohepten-5-one and N,N-dimethylamino-ethylamine, there is obtained 3-chloro-N-(2-dimethylamino-ethyl)-10,11-dihydro-5H-dibenzo[a,d]cyclohepten-5-imine (main isomer of the mixture), melting point 212°–214° C. (hydrochloride);

from 10-acetamido-10,11-dihydro-5H-dibenzo[a,d]cyclohepten-5-one and N,N-dimethylamino-ethylamine, there is obtained 10-acetamido-N-(2-dimethylamino-ethyl)-10,11-dihydro-5H-dibenzo[a,d]cyclohepten-5-imine, melting point at ca. 150° C. (dihydrochloride);

from 3-chloro-10,11-dihydro-5H-dibenzo[a,d]cyclohepten-5-one and N-morpholino-ethylamine, there is obtained 3-chloro-N-(2-morpholino-ethyl)-10,11-dihydro-5H-dibenzo[a,d]cyclohepten-5-imine, melting point 184°–187° C. (dihydrochloride);

from 10,11-dihydro-1-methoxy-5H-dibenzo[a,d]cyclohepten-5-one and N,N-dimethylamino-ethylamine, there is obtained 10,11-dihydro-N-(2-dimethylamino-ethyl)-1-methoxy-5H-dibenzo[a,d]cyclohepten-5-imine, melting point at ca. 100° C. (oxalate);

from 2-chloro-10,11-dihydro-5H-dibenzo[a,d]cyclohepten-5-one and N,N-dimethylamino-ethylamine, there is obtained 2-chloro-N-(2-dimethylamine-ethyl)-10,11-dihydro-5H-dibenzo[a,d]cyclohepten-5-imine, melting point 109°–112° C. (oxalate);

from 1-fluoro-10,11-dihydro-5H-dibenzo[a,d]cyclohepten-5-one and N,N-dimethylamino-ethylamine, there is obtained 1-fluoro-N-(2-dimethylamino-ethyl)-10,11-dihydro-5H-dibenzo[a,d]cyclohepten-5-imine, melting point 185°–188° C. (oxalate);

from 3-chloro-10,11-dihydro-5H-dibenzo[a,d]cyclohepten-5-one and N,N-dimethylamino-propylamine there is obtained 3-chloro-N-(3-dimethylamino-propyl)-10,11-dihydro-5H-dibenzo[a,d]cyclohepten-5-imine (main isomer of the mixture), melting point 274°–277° C. (dihydrochloride);

from 3-chloro-10,11-dihydro-5H-dibenzo[a,d]cyclohepten-5-one and N-(4-methylpiperazino)-ethylamine, there is obtained 3-chloro-N-[2-(4-methylpiperazino)-ethyl]-10,11-dihydro-5H-dibenzo[a,d]cyclohepten-5-imine, melting point 246°–248° C. (dioxolate);

from 3-bromo-10,11-dihydro-5H-dibenzo[a,d]cyclohepten-5-one and N,N-dimethylamino-ethylamine, there is obtained 3-bromo-N-(2-dimethylamino-ethyl)-10,11-dihydro-5H-dibenzo[a,d]cyclohepten-5-imine, melting point 215°–218° C. (hydrochloride);

from 3-bromo-10,11-dihydro-5H-dibenzo[a,d]cyclohepten-5-one and N,N-dimethylamino-ethylamine, there is obtained 3-bromo-N-(2-dimethylamino-ethyl)-10,11-dihydro-5H-dibenzo[a,d]cyclohepten-5-imine (main isomer of the mixture), melting point 180°–183° C. (dihydrochloride);

from 3-methoxy-carbonyl-10,11-dihydro-5H-dibenzo[a,d]cyclohepten-5-one and N,N-dimethylamino-ethylamine, there is obtained 3-methoxycarbonyl-N-(2-dimethylamino-ethyl)-10,11-dihydro-5H-dibenzo[a,d]cyclohepten-5-imine, melting point 161°–164° C. (oxalate);

from dibenzo[b,e]thiepin-11(6H)-one and N,N-dimethylamino-ethylamine, there is obtained N-(2-dimethylamino-ethyl)-dibenzo[b,e]thiepin-11(6H)-imine, melting point 179°–182° C., (oxalate);

from 1,3-dichloro-10,11-dihydro-5H-dibenzo[a,d]cyclohepten-5-one and N,N-dimethylamino-ethylamine, there is obtained 1,3-dichloro-N-(2-dimethylamino-ethyl)-10,11-dihydro-5H-dibenzo[a,d]cyclohepten-5-imine (trans isomer), melting point 209°–211° C. (dihydrochloride);

from 1,3-dichloro-10,11-dihydro-5H-dibenzo[a,d]cyclohepten-5-one and N,N-dimethylamino-ethylamine, there is obtained 1,3-dichloro-N-(2-dimethylamino-ethyl)-10,11-dihydro-5H-dibenzo[a,d]cyclohepten-5-imine, melting point 144°–147° C. (hydrochloride);

from 1-chloro-10,11-dihydro-7,8-dimethyl-5H-dibenzo[a,d]cyclohepten-5-one and N,N-dimethylamino-ethylamine, there is obtained 1-chloro-7,8-dimethyl-N-(2-dimethylamino-ethyl)-10,11-dihydro-5H-dibenzo[a,d]cyclohepten-5-imine, melting point 243°–246° C. (hydrochloride);

from 3-cyano-10,11-dihydro-5H-dibenzo[a,d]cyclohepten-5-one and N,N-dimethylamino-ethylamine, there is obtained 3-cyano-N-(2-dimethylamino-ethyl)-10,11-dihydro-5H-dibenzo[a,d]cyclopenten-5-imine; melting point 242°–244° C. (hydrochloride).

from 10(or 11)-bromo-1-chloro-5H-dibenzo[a,d]cyclohepten-5-one and N,N-dimethylamino-ethylamine, there is obtained 10(or 11)-bromo-1-chloro-N-(2-dimethylamino-ethyl)-5H-dibenzo[a,d]cyclohepten-5-imine, melting point 191°–193° C. (oxalate); and from 1,10(or 11)-dichloro-5H-dibenzo[a,d]cyclohepten-5-one and N,N-dimethylamino-ethylamine, there is obtained 1,10(or 11)-dichloro-N-(2-dimethylamino-ethyl)-5H-dibenzo[a,d]cyclohepten-5-imine, melting point 183°–185° C. (oxalate).

The 3-methoxycarbonyl-10,11-dihydro-5H-dibenzo[a,d]cyclohepten-5-one starting material mentioned hereinbefore can be prepared, for example, as follows:

4.6 g. of 3-cyano-10,11-dihydro-5H-dibenzo[a,d]cyclohepten-5-one, together with 4.5 g. of potassium hydroxide, 15 ml. of ethylene glycol and 5 ml. of water are heated to boiling under reflux conditions for 48 hours. The resulting solution is cooled diluted with water and extracted with ether. The aqueous phase is adjusted to a pH 1 by addition of 3N hydrochloric acid and extracted with chloroform. The chloroform extract is dried over sodium sulfate and evaporated. The residual 3-carboxy-10,11-dihydro-5H-dibenzo[a,d]cyclohepten-5-one melts at 221°–223° C.

8.8 g. of 3-carboxy-10,11-dihydro-5H-dibenzo[a,d]cyclohepten-5-one, together with 110 ml. of methanol and 600 ml. of absolute benzene, are heated in a Soxhlet apparatus filled with a molecular sieve (pore diameter 4A) for 12 hours. The resulting mixture is evaporated and the residue is taken up in ether. The extract is washed with 3N sodium hydroxide solution, dried over sodium sulfate and evaporated. The residual 3-methoxycarbonyl-10,11-dihydro-5H-dibenzo[a,d]cyclohepten-5-one melts at 109°–111° C.

The 3-cyano-10,11-dihydro-5H-dibenzo[a,d]cyclohepten-5-one starting material mentioned hereinbefore can be prepared as follows:

7.2 g. of 3-bromo-10,11-dihydro-5H-dibenzo[a,d]cyclohepten-5-one, together with 2.7 g. of copper cyanide and 10 ml. of dimethylformamide, are heated to boiling under reflux conditions for 6 hours. The resulting hot solution is poured into a solution containing 10 g. of iron trichloride in 15 ml. of water and 3 ml. of concentrated hydrochloric acid, stirred at 70° C. for 20 minutes and extracted with toluene. The toluene extract is washed first with 3N hydrochloric acid and then with 3N caustic soda, dried over sodium sulfate and evaporated. The 3-cyano-10,11-dihydro-5H-dibenzo[a,d]cyclohepten-5-one which is obtained, is purified by adsorption on the 10-fold amount of Kieselgel (eluting agent: toluene); melting point 104°–106° C.

EXAMPLE 2

Preparation of
3-chloro-N-(3-methylamino-propyl)-10,11-dihydro-5H-dibenzo[a,d]cyclohepten-5-imine oxalate 12.1 g. of 3-chloro-10,11-dihydro-5H-dibenzo[a,d]cyclohepten-5-one are dissolved in 700 ml. of absolute benzene at room temperature under an atmosphere of argon with stirring. After the addition of 44 g. of methylamino-propylamine, the solution is cooled to 5° C. and treated dropwise with a solution of 9 ml. of titanium tetrachloride in 40 ml. of absolute benzene. The resulting mixture is stirred at room temperature for 48 hours, heated under reflux conditions for 6 hours and subsequently concentrated to half volume. The concentrate is treated with water. The precipitate which forms is removed by filtration and washed several times with benzene. The aqueous phase is extracted with ether. The organic extracts are combined, washed with a saturated aqueous sodium chloride solution, dried over sodium sulfate and evaporated. The 3-chloro-N-(3-methylamino-propyl)-10,11-dihydro-5H-dibenzo[a,d]cyclohepten-5-imine which is obtained is purified by adsorption on a 20-fold amount of neutral aluminum oxide (activity grade II, eluting agent: benzene), dissolved in acetone and treated with a solution of 3.8 g. of oxalic acid in 40 ml. of ethanol. The oxalate which precipitates in crystalline form melts at 164°–167° C. after recrystallization from acetone/methanol.

The 3-chloro-N-(3-methylamino-propyl)-10,11-dihydro-5H-dibenzo[a,d]cyclohepten-5-imine oxalate is obtained as a stereoisomeric mixture in the ratio of about 3:1. The two isomers can be separated by thin layer chromatography (adsorbent: aluminum oxide Merck F 254, eluting agent: acetone/toluene/diethylamine 49:49:2).

In an analogous manner, utilizing the procedure of Example 2:

from 3-chloro-10,11-dihydro-5H-dibenzo[a,d]cyclohepten-5-one and ethylamino-propylamine, there is obtained 3-chloro-N-(3-ethylamino-propyl)-10,11-dihydro-5H-dibenzo[a,d]cyclohepten-5-imine, melting point 169°–172° C. (oxalate);

from 1-chloro-10,11-dihydro-5H-dibenzo[a,d]cyclohepten-5-one and methylamino-propylamine, there is obtained 1-chloro-N-(3-methylamino-propyl)-10,11-dihydro-5H-dibenzo[a,d]cyclohepten-5-imine, melting point 146°–149° C. (oxalate);

from 1-chloro-10,11-dihydro-5H-dibenzo[a,d]cyclohepten-5-one and ethylamino-propylamine, there is obtained 1-chloro-N-(3-ethylamino-propyl)-10,11-dihydro-5H-dibenzo[a,d]cyclohepten-5-imine, melting point 170°–173° C. (oxalate);

from 1-methyl-10,11-dihydro-5H-dibenzo[a,d]cyclohepten-5-one and ethylamino-propylamine, there is obtained 1-methyl-N-(3-ethylamino-propyl)-10,11-dihydro-5H-dibenzo[a,d]cyclohepten-5-imine, melting point 161°–163° C. (oxalate);

from 1-cyano-10,11-dihydro-5H-dibenzo[a,d]cyclohepten-5-one and ethylamino-propylamine, there is obtained 1-cyano-N-(3-ethylamino-propyl)-10,11-dihydro-5H-dibenzo[a,d]cyclohepten-5-imine, melting point 129°–132° C. (oxalate);

from 10,11-dihydro-5H-dibenzo[a,d]cyclohepten-5-one and ethylamino-propylamine, there is obtained N-(3-ethylamino-propyl)-10,11-dihydro-5H-dibenzo[a,d]cyclohepten-5-imine, melting point 174°–176° C. (oxalate); and from 10,11-dihydro-5H-dibenzo[a,d]cyclohepten-5-one and N-methylamino-propylamine, there is obtained N-(3-methylamino-propyl)-10,11-dihydro-5H-dibenzo[a,d]cyclohepten-5-imine, melting point 198°–201° C. (oxalate).

EXAMPLE 3

Preparation of N-(2-dimethylamino-ethyl)-5H-dibenzo[a,d]cyclohepten-5-imine oxalate 15.5 g. of 5H-dibenzo[a,d]cyclohepten-5-one are dissolved in 300 ml. of absolute benzene with stirring at room temperature and under an atmosphere of argon. Following the addition of 66 g. of N,N-dimethylamino-ethylamine, the solution is cooled to 0° C. and treated dropwise with a solution of 5.4 ml. of titanium tetrachloride in 40 ml. of absolute benzene. The reaction mixture is stirred at room temperature for 48 hours and then filtered. The filtrate is evaporated under reduced pressure. The residue is treated with ice and 3N hydrochloric acid and exhaustively extracted with ether. The ether extract is washed first with water, then with a saturated aqueous sodium chloride solution, dried over sodium sulfate and evaporated. The residual N-(2-dimethylamino-ethyl)-5H-dibenzo[a,d]cyclohepten-5-imine is taken up in acetone and treated with a solution of 2.8 g. of oxalic acid in 40 ml. of ethanol. The oxalate which precipitates in crystalline form melts at 177°–179° C., after recrystallization from acetone/methanol.

In an analogous manner, utilzing the procedure of Example 3:

from 5H-dibenzo[a,d]cyclohepten-5-one and N,N-dimethyl-amino-propylamine, there is obtained N-(3-dimethylamino-propyl)-5H-dibenzo[a,d]cyclohepten-5-imine, melting point 159°–161° C. (oxalate);

from 5H-dibenzo[a,d]cyclohepten-5-one and N,N-diethylamino-ethylamine, there is obtained N-(2-diethylamino-ethyl)-5H-dibenzo[a,d]cyclohepten-5-imine, melting point 115°–118° C. (oxalate);

from 5H-dibenzo[a,d]cyclohepten-5-one and N,N-diethylamino-propylamine, there is obtained N-(3-diethylamino-propyl)-5H-dibenzo[a,d]cyclohepten-5-imine, melting point 139°–140° C. (oxalate);

from 10-bromo-5H-dibenzo[a,d]cyclohepten-5-one and N,N-dimethylamino-ethylamine, there is obtained 10-bromo-N-(2-dimethylamino-ethyl)-5H-dibenzo[a,d]cyclohepten-5-imine, melting point 173°–174° C. (oxalate);

from 5H-dibenzo[a,d]cyclohepten-5-one and methylamino-propylamine, there is obtained N-(3-methylamino-propyl)-5H-dibenzo[a,d]cyclohepten-5-imine, melting point 151°–154° C. (oxalate);

from 5H-dibenzo[a,d]cyclohepten-5-one and ethylamino-propylamine, there is obained N-(3-ethylamino-propyl)-5H-dibenzo[a,d]cyclohepten-5-imine, melting point 158°–160° C. (oxalate);

from 10-cyano-5H-dibenzo[a,d]cyclohepten-5-one and N,N-dimethylamino-ethylamine, there is obtained 10-cyano-N-(2-dimethylamino-ethyl)-5H-dibenzo[a,d]cyclohepten-5-imine, melting point 187°–189° C. (oxalate);

from 3-chloro-5H-dibenzo[a,d]cyclohepten-5-one and N,N-dimethylamino-ethylamine, there is obained 3-chloro-N-(2-dimethylamino-ethyl)-5H-dibenzo[a,d]cyclohepten-5-imine, melting point 173°–175° C. (oxalate);

from 10-(N,N-dimethyl-sulfonamido)-5H-dibenzo[a,d]cyclohepten-5-one and N,N-dimethylamino-ethylamine, there is obtained N-(2-dimethylamino-ethyl)-10-(N,N-dimethyl-sulfonamido)-5H-dibenzo[a,d]cyclohepten-5-imine, melting point 194°–196° C. (oxalate) and from 1-chloro-5H-dibenzo[a,d]cyclohepten-5-one and N,N-dimethylamino-ethylamine, there is obtained 1-chloro-N-(2-dimethylamino-ethyl)-5H-dibenzo[a,d]cyclohepten-5-imine, melting point 166°–169° C. (oxalate).

EXAMPLE 4

Preparation of 2-chloro-N-(2-dimethylamino-ethyl)-thioxanthen-9-imine oxalate 18.6 g. of 2-chloro-thioxanthen-9-one are dissolved in 350 ml. of absolute toluene with stirring at room temperature under an atmosphere of argon. After the addition of 60 g. of N,N-dimethylamino-ethylamine, the solution is cooled to 0° C. and treated dropwise over a period of 30 minutes with a solution of 5 ml. of titanium tetrachloride in 50 ml. of absolute toluene. The resulting mixture is stirred at room temperature for 76 hours and then filtered. The filtrate is concentrated under reduced pressure. The concentrate is treated with ice-water and exhaustively extracted with methylene chloride. The methylene chloride extract is washed first with water, then with a saturated aqueous sodium chloride solution, dried over sodium sulfate and evaporated. The 2-chloro-N-(2-dimethylamino-ethyl)-thioxanthen-9-imine which is obtained is taken up in acetone and treated with a solution of 6 g. of oxalic acid in 50 ml. of ethanol. The oxalate which precipitates in crystalline form melts at 181°–183° C. after drying in vacuum.

In an analogous manner, utilizing the procedure of Example 4:

from 2-chloro-thioxanthen-9-one and N,N-dimethylamino-propylamine, there is obtained 2-chloro-N-(3-dimethylamino-propyl)-thioxanthen-9-imine, melting point 176°–179° C. (oxalate);

from 2-chloro-thioxanthen-9-one and N,N-diethylamino-ethylamine, there is obtained 2-chloro-N-(2-diethylamino-ethyl)-thioxanthen-9-imine, melting point 171°–173° C. (oxalate); and from 2-chloro-thioxanthen-9-one and N,N-diethylamino-propylamine, there is obtained 2-chloro-N-(3-diethylamino-propyl)-thioxanthen-9-imine, melting point 144°–146° C. (oxalate).

EXAMPLE 5

Preparation of
N-(3-dimethylamino-propyl)-10,11-dihydro-5H-dibenzo[a,d]cyclohepten-5-imine oxalate 5.2 g. of 10,11-dihydro-5H-dibenzo[a,d]cyclohepten-5-one are dissolved in 200 ml. of absolute benzene with stirring at room temperature under an atmosphere of argon. After the addition of 23 g. of N,N-dimethylamino-propylamine, the solution is treated with 4.5 g. of aluminum chloride. The resulting mixture is stirred first at room temperature for 20 hours, then heated to boiling under reflux conditions for 12 hours and subsequently concentrated and exhaustively extracted with ether. The ether extract is washed with a saturated aqueous sodium chloride solution, dried over sodium sulfate and evaporated under reduced pressure. N-(3-dimethylamino-propyl)-10,11-dihydro-5H-dibenzo[a,d]cyclohepten-5-imine, which is obtained, is taken up in acetone and treated with a solution of 1.2 g. of oxalic acid in 20 ml. of ethanol. The oxalate which precipitates in crystalline form melts at 150°–152° C.

EXAMPLE 6

Preparation of
N-(3-dimethylamino-propyl)-10,11-dihydro-5H-dibenzo[a,d]cyclohepten-5-imine oxalate 10.8 g. of 10,11-dihydro-5H-dibenzo[a,d]cyclohepten-5-one are dissolved in 200 ml. of absolute toluene with stirring at room temperature under an atmosphere of argon. After the addition of 38 g. of N,N-dimethylamino-propylamine, the solution is cooled to 0° C. and treated dropwise with 10 g. of antimony pentachloride. After the solution warms to room temperature, the resulting mixture is stirred at 90° C. for 7 hours. Thereafter, the solution is evaporated to half the volume, hydrolyzed by addition of water and filtered. The filtrate is extracted several times with ether. The combined ethereal solutions are washed with 2N hydrochloric acid. The aqueous phase is made alkaline and extracted with ether. The ether extract is washed with a saturated sodium chloride solution, dried over sodium sulfate and evaporated. The N-(3-dimethylamino-propyl)-10,11-dihydro-5H-dibenzo[a,d]cyclohepten-5-imine which is obtained is dissolved in acetone and treated with a solution of 2.25 g. of oxalic acid in 35 ml. of ethanol. The oxalate which precipitates in crystalline form melts at 150°–152° C. after recrystallization from acetone.

EXAMPLE 7

Preparation of
N-(3-dimethylamino-propyl)-10,11-dihydro-5H-dibenzo[a,d]cyclohepten-5-imine oxalate 2.6 g. of 10,11-dihydro-5H-dibenzo[a,d]cyclohepten-5-one are dissolved in 100 ml. of toluene with stirring at room temperature under an atmosphere of argon. After the addition of 11.5 g. of N,N-dimethylamino-propylamine, the solution is cooled to 0° C. and treated slowly with 3.9 g. of antimony trichloride. After the solution warms to room temperature, the resulting mixture is stirred at 80° C. for 6 hours and worked up as described in Example 6. The N-(3-dimethylamino-propyl)-10,11-dihydro-5H-dibenzo[a,d]cyclohepten-5-imine which is obtained is dissolved in acetone and treated with a solution of 0.9 g. of oxalic acid in 20 ml. of ethanol. The oxalate which precipitates in crystalline form melts at 150°–152° C. after recrystallization.

EXAMPLE 8

Preparation of
N-(2-dimethylamino-propyl)-10,11-dihydro-5H-dibenzo[a,d]cyclohepten-5-imine oxalate 10.4 g. of 10,11-dihydro-5H-dibenzo[a,d]cyclohepten-5-one are treated with 6.12 g. of N,N-dimethylamino-propylamine in 20 ml. of absolute toluene. After the addition of 20 g. of a 4A molecular sieve (bead form) the solution is heated under reflux conditions for 20 hours. The molecular sieve is then removed by filtration. The filtrate is evaporated. The residue is taken up with ice and 3N hydrochloric acid and extracted with ether. The aqueous phase is made alkaline and extracted with ether. The combined ether extracts are washed with water and concentrated sodium chloride solution, dried over sodium sulfate and evaporated under reduced pressure. The N-(2-dimethylamino-propyl)-10,11-dihydro-5H-dibenzo[a,d]cyclohepten-5-imine which is obtained is dissolved in acetone and treated with an equivalent amount of oxalic acid in acetone. The oxalate which precipitates in crystalline form melts at 150°–152° C.

EXAMPLE 9

Preparation of
1-chloro-N-(2-methylamino-ethyl)-10,11-dihydro-5H-dibenzo[a,d]cyclohepten-5-imine oxalate 7.3 g. of 1-chloro-10,11-dihydro-5H-dibenzo[a,d]cyclohepten-5-one and 45 g. of N-methylethylenediamine are heated overnight to 200° C. under an atmosphere of nitrogen in a pressure flask. After evaporation of the excess amine, the concentrate is treated with ice and 3N hydrochloric acid. The unreacted ketone is extracted with ether. The aqueous phase is then made alkaline and extracted with ether. The ether extract is washed with a saturated aqueous sodium chloride solution, dried over sodium sulfate and evaporated. The 1-chloro-N-(2-methylamino-ethyl)-10,11-dihydro-5H-dibenzo[a,d]cyclohepten-5-imine which is obtained, is dissolved in acetone and treated with an equivalent amount of hydrochloric acid in ether. The hydrochloride which precipitates in crystalline form melts at 221°–224° C. after recrystallization from acetone/methanol.

In an analogous manner, utilizing the procedure of Example 9:

from 3-chloro-10,11-dihydro-5H-dibenzo[a,d]cyclohepten-5-one and N-methylamino-ethylamine, there is obtained 3-chloro-N-(2-methylamino-ethyl)-10,11-dihydro-5H-dibenzo[a,d]cyclohepten-5-imine, melting point 202°–204° C. (hydrochloride);

from 10,11-dihydro-5H-dibenzo[a,d]cyclohepten-5-one and N-methylamino-ethylamine, there is obtained N-(2-methylamino-ethyl)-10,11-dihydro-5H-dibenzo[a,d]cyclohepten-5-imine, melting point 211°–213° C. (hydrochloride);

from 1-chloro-10,11-dihydro-5H-dibenzo[a,d]cyclohepten-5-one and 1-dimethylamino-2-propylamine, there is obtained 1-chloro-N-(2-dimethylamino-1-methyl-ethyl)-10,11-dihydro-5H-dibenzo[a,d]cyclohepten-5-imine, melting point 197°–200° C. (hydrochloride);

from 1-chloro-10,11-dihydro-5H-dibenzo[a,d]cyclohepten-5-one and ethylenediamine, there is obtained 1-chloro-N-(2-amino-ethyl)-10,11-dihydro-5H-dibenzo[a,d]cyclohepten-5-imine, melting point 149°–150° C. (maleate);

from 10,11-dihydro-5H-dibenzo[a,d]cyclohepten-5-one and ethylenediamine, there is obtained N-(2-amino-ethyl)-10,11-dihydro-5H-dibenzo[a,d]cyclohepten-5-imine, melting point 201°–202° C. (hydrochloride);

from 3-dimethylcarbamoyl-10,11-dihydro-5H-dibenzo[a,d]cyclohepten-5-one and N,N-dimethylamino-ethylamine, there is obtained 3-dimethylcarbamoyl-N-(2-dimethylamino-ethyl)-10,11-dihydro-5H-dibenzo[a,d]cyclohepten-5-imine; and from 3-chloro-10,11-dihydro-5H-dibenzo[a,d]cyclohepten-5-one and ethylenediamine, there is obtained 3-chloro-N-(2-amino-ethyl)-10,11-dihydro-5H-dibenzo[a,d]cyclohepten-5-imine, melting point 226°–228° C. (hydrochloride).

EXAMPLE 10

Preparation of N-(2-pyrrolidino-ethyl)-10,11-dihydro-5H-dibenzo[a,d]cyclohepten-5-imine oxalate 20 g. of N-(2-tosyloxy-ethyl)-10,11-dihydro-5H-dibenzo[a,d]cyclohepten-5-imine are dissolved in 180 ml. of toluene and, after the addition of 12.3 ml. of pyrrolidine, heated to boiling under reflux conditions for 15 minutes. Subsequently, the resulting mixture is evaporated under reduced pressure. The residue is partitioned between ether and water. The ether phase is separated, washed, dried and evaporated. The oily N-(2-pyrrolidino-ethyl)-10,11-dihydro-5H-dibenzo[a,d]cyclohepten-5-imine which is obtained, may be converted into the maleate which has a melting point of 145°–146° C.

In an analogous manner, utilizing the procedure of Example 10:

from N-(2-tosyloxy-ethyl)-10,11-dihydro-5H-dibenzo[a,d]cyclohepten-5-imine and piperidine, there is obtained N-(2-piperidino-ethyl)-10,11-dihydro-5H-dibenzo[a,d]cyclohepten-5-imine, melting point 140°–141° C. (maleate);

from N-(2-toxyloxy-ethyl)-10,11-dihydro-5H-dibenzo[a,d]cyclohepten-5-imine and dimethylamine, there is obtained N-(2-dimethylamino-ethyl)-10,11-dihydro-5H-dibenzo[a,d]cyclohepten-5-imine, melting point 131°–132° C. (maleate);

from N-(2-tosyloxy-ethyl)-10,11-dihydro-5H-dibenzo-[a,d]cyclohepten-5-imine and diethylamine, there is obtained N-(2-diethylamino-ethyl)-10,11-dihydro-5H-dibenzo[a,d]cyclohepten-5-imine, melting point 125°–126° C. (oxalate); and from N-(2-tosyloxy-ethyl)-10,11-dihydro-5H-dibenzo[a,d]cyclohepten-5-imine and hydroxypropyl-piperazine, there is obtained N-[2-(4-hydroxypropyl-piperazino)-ethyl]-10,11-dihydro-5H-dibenzo[a,d]cyclohepten-5-imine, melting point 136°–140° C. (dimaleate).

The N-(2-tosyloxy-ethyl)-10,11-dihydro-5H-dibenzo[a,d]cyclohepten-5-imine employed as the starting material can be prepared as follows:

600 ml. of ethanolamine are added to 208 g. of 10,11-dihydro-5H-dibenzo[a,d]cyclohepten-5-one. The mixture is heated under reflux conditions in an inert gas atmosphere for 16 hours. The refluxing ethanolamine is recycled into the reaction vessel through a Soxhlet attachment filled with 2 × 130 g. of 4A molecular sieve (bead form, 2 mm; Merck). The resulting mixture is then evaporated. The residue is dissolved in ether. The ether solution is washed with water and extracted with ice-cold 1N nitric acid. The acid extracts are washed with ether, adjusted to a pH value of 10–12 by addition of cold concentrated sodium hydroxide solution and subsequently extracted with methylene chloride. The methylene chloride extract is washed with water, dried over calcium chloride and evaporated under reduced pressure. The N-(2-hydroxy-ethyl)-10,11-dihydro-5H-dibenzo[a,d]cyclohepten-5-imine which is obtained melts at 93°–94° C. after recrystallization from acetone/petroleum ether: 3:5.

A solution of 150 g. of N-(2-hydroxy-ethyl)-10,11-dihydro-5H-dibenzo[a,d]cyclohepten-5-imine in 1000 ml. of absolute benzene and 165 ml. of triethylamine is treated dropwise at 5°–10° C. over a period of 30 minutes with a solution of 119.5 g. of p-toluenesulfonyl chloride in 500 ml. of absolute benzene. The resulting mixture is stirred at room temperature for 48 hours, then poured onto ice-water. The benzene phase is separated, washed, dried and evaporated. The N-(2-toxyloxy-ethyl)-10,11-dihydro-5H-dibenzo[a,d]cyclohepten-5-imine which is obtained melts at 114°–116° C. after recrystallization from ethanol.

The following Examples illustrate several pharmaceutical formulations containing the tricyclic imines of the invention:

EXAMPLE 11

Tablets of the following composition are prepared:

| | |
|---|---|
| 3-chloro-N-(2-dimethylamino-ethyl)-10,11-dihydro-5H-dibenzo[a,d]cyclohepten-5-imine | 10 mg. |
| lactose | 63 mg. |
| corn starch | 74 mg. |
| talcum | 2.7 mg. |
| magnesium stearate | 0.3 mg. |
| | 150 mg. |

The active ingredient is mixed with lactose and the corn starch and granulated with the aid of ethanol. The granulate is dried and, after the addition of talcum, compressed into tablets.

EXAMPLE 12

Capsules of the following composition are prepared:

| | |
|---|---|
| N-(2-dimethylamino-ethyl)-5H-dibenzo[a,d]cyclohepten-5-imine | 25 mg. |
| lactose | 150 mg. |
| corn starch | 30 mg. |
| talcum | 5 mg. |
| | 210 mg. |

The active ingredient is homogeneously mixed with the adjuvants, passed through a sieve (mesh-width 0.23 mm.) and filled into gelatin capsules.

EXAMPLE 13

Dragees of the following composition are prepared:

| | |
|---|---|
| 1-chloro-N-(2-dimethylamino-ethyl)-10,11-dihydro-5H-dibenzo[a,d]cyclohepten-5-imine | 25 mg. |
| mannitol | 100 mg. |
| corn starch | 20 mg. |
| talcum | 5 mg. |
| | 150 mg. |

The active ingredient is passed through a sieve (mesh-width 0.23 mm.) with the mannitol. A 10 percent aqueous paste is prepared from the corn starch and homogeneously mixed with the mannitol/active ingredient mixture. The moist mass is passed through a sieve (mesh-width 1.0 mm.). The granulate obtained is dried and, after the addition of talcum, compressed to cores which are coated with a sugar layer in conventional manner by dredging.

EXAMPLE 14

Tablets of the following composition are prepared:

| | |
|---|---|
| 1-bromo-N-(2-dimethylamino-ethyl)-10,11-dihydro-5H-dibenzo[a,d]cyclohepten-5-imine | 10 mg. |
| silicic acid | 25 mg. |
| lactose | 115 mg. |
| corn starch | 50 mg. |

-continued

| | |
|---|---|
| calcium stearate | 10 mg. |
| | 210 mg. |

The active ingredient is well mixed with the other adjuvants granulated and compressed into tablets.

We claim:

1. A compound of the formula

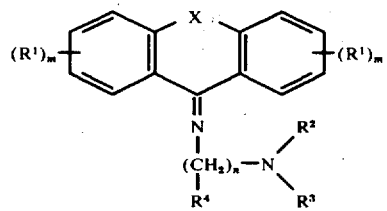

wherein X is thiomethylene; $R^1$ is hydrogen or lower alkyl; $R^2$ and $R^3$, individually, are hydrogen or lower alkyl; $R^4$ is hydrogen or lower alkyl; and $n$ is an integer from 2 to 5; and $m$ is an integer from 1 to 3, or a pharmaceutically acceptable acid addition salt thereof.

2. In accordance with claim 1, a compound of the formula

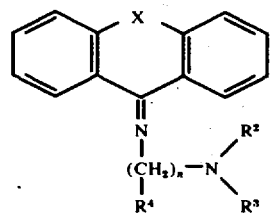

wherein X is thiomethylene; $R^2$ and $R^3$, individually, are lower alkyl; $R^4$ is hydrogen; and $n$ is 2 or 3, or a pharmaceutically acceptable acid addition salt thereof.

3. A compound in accordance with claim 2, N-(2-dimethyl-amino-ethyl)-dibenzo[b,e]thiepin-11(6H)-imine.

* * * * *